(12) United States Patent
Rockney

(10) Patent No.: US 8,094,305 B2
(45) Date of Patent: Jan. 10, 2012

(54) EFFICIENT OPTICAL ARRANGEMENT FOR ILLUMINATION AND DETECTION OF LABEL-FREE BIOSENSORS AND METHOD TO REDUCE INTERFERENCE FRINGES IN LABEL-FREE IMAGING

(75) Inventor: Bennett H. Rockney, Westford, MA (US)

(73) Assignee: SRU Biosystems, Inc., Woburn, MA (US)

( * ) Notice: Subject to any disclaimer, the term of this patent is extended or adjusted under 35 U.S.C. 154(b) by 305 days.

(21) Appl. No.: 12/586,702

(22) Filed: Sep. 25, 2009

(65) Prior Publication Data
US 2010/0195099 A1 Aug. 5, 2010

Related U.S. Application Data

(60) Provisional application No. 61/206,676, filed on Feb. 2, 2009.

(51) Int. Cl.
*G01J 3/28* (2006.01)

(52) U.S. Cl. ...................................... 356/326

(58) Field of Classification Search ........................ None
See application file for complete search history.

(56) References Cited

U.S. PATENT DOCUMENTS

| | | | |
|---|---|---|---|
| 6,870,630 B2 | 3/2005 | Budach et al. | 356/521 |
| 6,990,259 B2 | 1/2006 | Cunningham | 385/12 |
| 7,286,221 B2 | 10/2007 | Caracci et al. | 356/300 |
| 7,292,336 B2 | 11/2007 | Cunningham et al. | 356/326 |
| 7,575,939 B2 | 8/2009 | Cunningham et al. | 436/524 |
| 2002/0127565 A1 | 9/2002 | Cunningham et al. | 435/6 |
| 2003/0027327 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |

FOREIGN PATENT DOCUMENTS

WO WO 2008/130278 A2 * 10/2008

OTHER PUBLICATIONS

PCT International Preliminary Report on Patentability mailed Aug. 11, 2011 in PCT Application No. PCT/US2009/005328.
Search Report and Written Opinion mailed Jan. 21, 2010 in PCT/US09/05328, filed Sep. 25, 2009.

* cited by examiner

*Primary Examiner* — F. L. Evans
(74) *Attorney, Agent, or Firm* — McDonnell Boehnen Hulbert & Berghoff LLP

(57) ABSTRACT

An optical arrangement for illuminating a surface of a biosensor is described. The biosensor is preferably a sensor having periodic surface grating structure. The arrangement includes a light source generating light, collimating optics for collimating the light from the light source, and first reflecting surface receiving light from the collimating optics and directing incident light onto a surface of the biosensor and a second spatially separated reflecting surface receiving light reflected from the surface of the biosensor. The arrangement further includes telecentric optics (e.g., telecentric lens) receiving light from the second surface of the prism. The telecentric lens directs light onto an entrance slit of a spectrometer. The arrangement increases the light collection efficiency at the spectrometer as compared to prior art arrangements. The use of an incoherent light source and an arrangement in which incident light impinges upon the biosensor surface at a non-normal angle of incidence parallel to the direction of the grating lines on the sensor eliminates undesirable interference fringes in peak wavelength value measurements of the sensor.

26 Claims, 4 Drawing Sheets

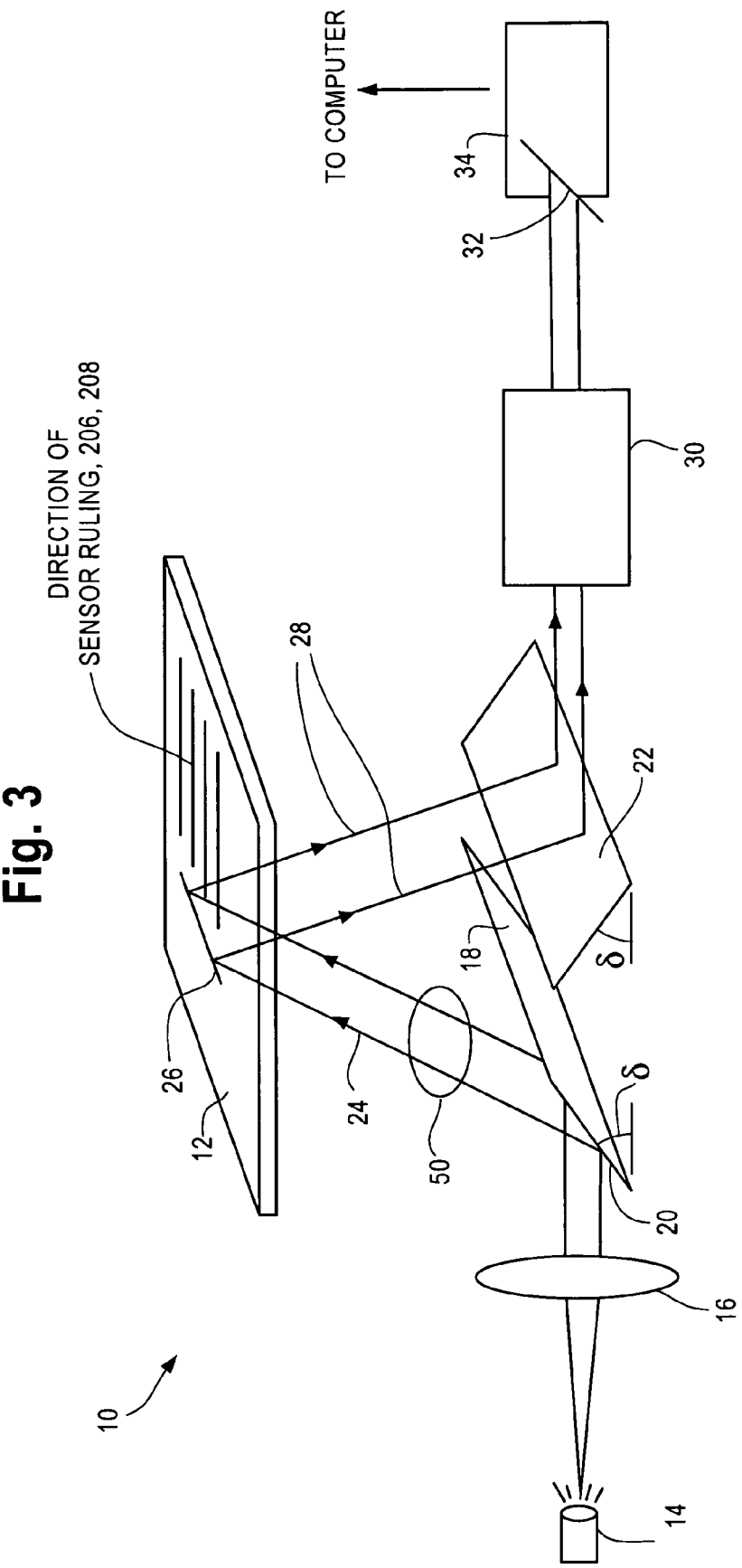

EFFICIENT OPTICAL ARRANGEMENT FOR ILLUMINATION AND DETECTION OF LABEL-FREE BIOSENSORS AND METHOD TO REDUCE INTERFERENCE FRINGES IN LABEL-FREE IMAGING

PRIORITY

This application claims priority benefits under 35 U.S.C. §119(e) to U.S. Provisional Application Ser. No. 61/206,676 filed Feb. 2, 2009.

BACKGROUND

This invention relates to optical arrangements for illumination of the surface of a optical biosensor and the detection of interactions, typically biochemical interactions, occurring on the surface of the biosensor.

The applicant's assignee SRU Biosystems, Inc. of Woburn, Mass. has developed and commercialized a label-free photonic crystal optical biosensor in which the surface of the biosensor includes a periodic surface grating. The biosensors are described in the patent literature, see for example U.S. patent application publications U.S. 2003/0027327; 2002/0127565, 2003/0059855 and 2003/0032039, the content of which is incorporated by reference herein.

SRU Biosystems has also developed a reading instrument for the biosensors. The reading instrument includes a light source (which can take the form of a white light source) and an optical arrangement for directing the light from the source to the surface of the biosensor at normal or near normal incidence. The optical arrangement also directs light reflected from the surface of the biosensor to a spectrometer or other instrument for detecting the peak wavelength (PWV) of the reflected light. Biochemical interactions occurring on the surface of the biosensor cause a change in the index of refraction of the biosensor surface, which results in a small shift in the PWV. The optical arrangements in the detection instrument are shown in the above patent documents. Briefly, the optical arrangement uses a 45-degree beam splitter cube to pass illumination upward to the biosensor and then to reflect light returning from the sensor to the spectrometer entrance slit. Each passage of the light through the beam splitter reduces the light intensity by half. Since the light passes through the beam splitter twice, there results an overall four-fold reduction in intensity of light impinging on the spectrometer.

This invention provides an optical arrangement for illumination and detection of a biosensor which eliminates the need for a beam splitter to direct the incident and reflected light. This increases the light efficiency four-fold as compared to the beam splitter arrangement described in the above-referenced patent documents.

SUMMARY

As explained in more detail below, an optical arrangement for illuminating a surface of a biosensor is described. The biosensor is preferably a sensor having a periodic surface grating structure, such as described in the above-referenced patent documents. However, other types of sensors having a grating structure can be used in conjunction with the present optical arrangement.

The arrangement includes a light source generating light, collimating optics for collimating the light from the light source, and first and second spatially separated reflecting surfaces, the first surface receiving light from the collimating optics and directing incident light onto a surface of the biosensor and the second surface receiving light reflected from the surface of the biosensor. The arrangement further includes telecentric optics (e.g., telecentric lens) receiving light from the second surface of the prism. The telecentric lens directs light onto an entrance slit of a spectrometer.

In one embodiment, the first and second spatially separated reflecting surfaces comprise two reflecting surfaces of a non-right angle prism. The surfaces can also take the form of two spatially separated mirrors. The surfaces (whether in the prism or mirror embodiment) are inclined at an angle that is shallower than 45 degrees.

Additionally, preferred embodiments are described below wherein the incident light impinges upon the biosensor surface at a non-normal angle of incidence, such as between about 6 and 12 degrees. The deviation from normal incidence is chosen to be parallel to the direction of the grating lines on the sensor. It has been discovered that with non-laser (incoherent) light sources in this arrangement (such as LED or arc lamp sources), undesirable interference fringes in the spectrum essentially disappear and thereby allows more precise measurements of the peak wavelength of reflected (or transmitted) light from the sensor to be obtained. In this regard, a method for reducing interference fringes produced in label-free imaging of a photonic crystal biosensor having a periodic grating structure in the form of lines having a direction is described, comprising the steps of: providing a light source generating incoherent light; directing the incoherent light through collimating optics and generating collimated the light from the light source; directing the collimated light onto a surface of the biosensor at a non-normal angle of incidence, and wherein the deviation from normal incidence is chosen to be parallel to the said direction of the lines of the periodic grating structure; directing light reflected from the biosensor to telecentric optics and directing light from the telecentric optics to a spectrometer.

BRIEF DESCRIPTION OF THE DRAWINGS

FIG. 3 is a schematic diagram of an alternative embodiment using two spatially separated mirrors for the spatially separated reflecting surfaces.

DETAILED DESCRIPTION

Figure 1:
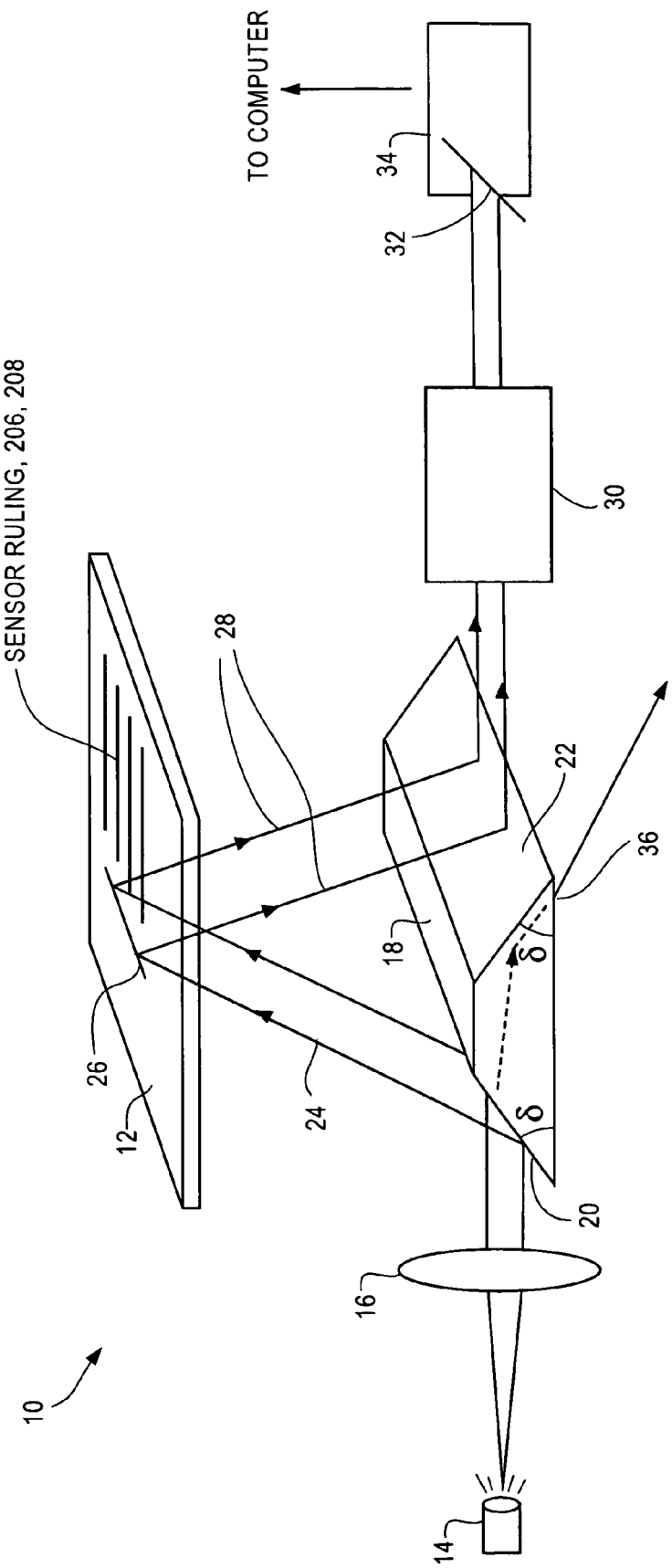
FIG. 1 is a schematic diagram of an optical arrangement for illuminating a biosensor in accordance with a presently preferred embodiment.

The optical arrangement for illuminating a biosensor in accordance with a first embodiment of this disclosure uses a non-right angle prism to illuminate the sensor and receive its reflected signal at an equal angle slightly off axis. A presently preferred arrangement 10 is shown in FIG. 1. The arrangement is used for illuminating a surface of a biosensor 12 having a periodic surface grating structure, which is shown in more detail in FIG. 2A. The biosensor 12 may take the form of a photonic crystal biosensor of the type described in the above-referenced patent literature. Other types of biosensors can be used as wells, such as those described in Wawro, U.S. Pat. No. 7,400,399, Duveneck et al., U.S. Pat. No. 6,395,558; Published PCT application. WO 98/09156; PCT/EP94/ 02361; and Budach et al., U.S. Pat. No. 6,707,561.

The arrangement 10 includes a light source 14 generating light. The light source 14 is preferably a quasi-point source, such as a Light Emitting Diode (LED). The light source could be a broad spectrum white light source or a narrow spectrum light source such as a laser light source emitting light in a narrow band of wavelengths.

The arrangement 10 further includes collimating optics 16 for collimating the light emitted from the light source 14.

Collimated light is directed onto the first of two spatially separated reflecting surfaces 20 and 22. In the embodiment of FIG. 1, the configuration includes a non-right angle prism 18. The prism 18 has a first reflecting surface 20 receiving light from the collimating optics 16 and directing incident light 24 onto a surface of the biosensor 12. The angle of inclination of the surfaces 20 and 22 (angle δ) from the direction of propagation of the light from the light source is less than 45 degrees, with angle δ shown typically having a value of say 40-44 degrees.

In this instance, the biosensor surface receiving the incident light 24 is the lower surface of the biosensor but the sensor could be illuminated from above. The incident light creates a resonance effect in the biosensor 12 as described in the above-reference patent literature. Parallel bundles of light 28 are reflected from the surface of the biosensor and are received by a second reflecting surface 22 of the prism 18. Light is reflected from the surface 22 towards telecentric optics (lens) 30. The telecentric lens 30 focuses the light on the entrance slit 32 of a spectrometer 34. The spectrometer can take a variety of forms, including an imaging spectrometer. The spectrometer 34 is coupled to a computer (not shown) for display and analysis of the peak wavelength values of the light detected by the spectrometer.

Figure 2A:
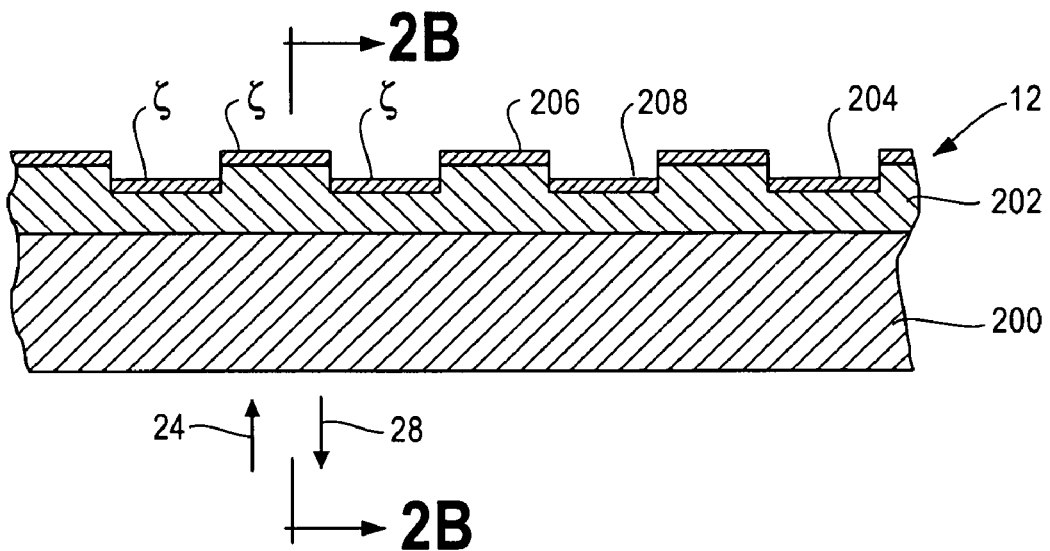
FIG. 2A is a cross-sectional view of the biosensor of FIG. 1 shown greatly enlarged, showing the incident and reflected light of FIG. 1.

As shown in FIG. 2A, a representative embodiment of the biosensor 12 includes a clear substrate layer 200 made from glass or polymeric material (e.g., polyethylene terepthalate), a grating layer 202 comprising a layer of relatively low index of refraction material having alternating high and low regions 206 and 208, forming a one-dimensional periodic grating extending into the plane of the page. A relatively high index of refraction material 204 such as $TiO_2$ is deposited on the surface of the periodic grating. The nature of the periodic surface grating can vary widely, for example the grating can be arranged as an array of posts and holes in a two dimensional arrangement, or in still other arrangements. Methods of manufacturing sensors such as shown in FIG. 2A using replica molding are known in the art, and therefore a discussion is omitted here in order to not obfuscate the present disclosure.

Figure 2B:
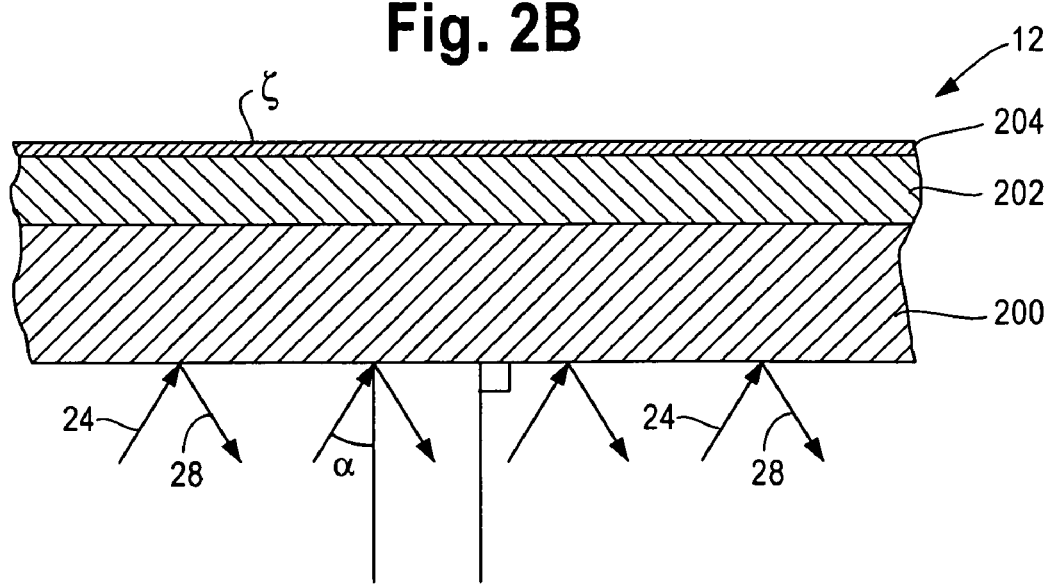
FIG. 2B is another cross section of the biosensor of FIG. 1 taken along the lines 2B-2B of FIG. 2A.

Referring to FIGS. 2A and 2B, the incident light 24 impinges on the lower surface of the biosensor 12 at an angle of incidence which departs for normal incidence by a small value, shown as angle α in FIG. 2B. The light reflects from the surface at an angle from normal which is equal to angle α. The values of angle α are preferably between 3 and 15 degrees, and more preferably between 6 and 10 degrees.

There are three problems to the geometry of FIG. 1 that can be solved by properly orienting the angle of incidence α, the direction of rulings of the grating (high and low areas 206 and 208) on the sensor surface, shown in FIG. 2A, and the slit 32 of the spectrometer 34.

One problem is that PWV measurements made by the spectrometer 34 show a parabolic dependence on the angle of the incident light 24 with respect to the orientation of the grating on the surface of the sensor. In particular, the sensor displays the parabolic dependence of reflected wavelength on the angle only for one axis of tilt, and that is tilt in a plane perpendicular to the grating rulings. In the orthogonal direction, where the plane of the tilt is parallel to the grating rulings, there is much reduced angular dependence of PWV measurements. It is preferred to operate with incident light oriented as close as possible to normal incidence, where the slope of the parabola is zero; as a result, small deviations in angle, such as those that may arise from deviations in the sensor's flatness, produce minimal variations in PWV measurements. Conversely, intentionally operating off-axis (incident light oriented at a non-normal angle of incidence) will establish an operating point where small variations in sensor angle will produce a large and undesirable PWV shift. A key in the arrangements of this disclosure is that the deviation from normal-incidence is chosen to be parallel to the direction of the grating lines on the sensor, as shown in FIG. 2B.

Another problem with operating off-axis is that different portions of the field of view will be a different distances from the telecentric lens 30, potentially resulting in the edges of the field of view being out of focus. But because the biosensor is being imaged on the spectrometer slit 32, only the portion of the field of view that maps to the slit 32 is important to the optical system. The slit preferably has a very high aspect ratio (greater than 100 to 1); it thus has very minimal spatial extent in one direction. If the reflecting prism 18 is oriented so that the angle of incidence α on the sensor deviates from normal through rotation around the slit's line image on the sensor (26 in FIG. 1) rather than parallel to the line image, differences in path length will be minimal across the usable field of view. (Typical images of the slit on the field of view will have a width one pixel wide, on the order of 5 μm to 10 μm.) As shown in FIGS. 1 and 2B, the image (26) of the entrance slit on the biosensor surface is oriented perpendicular to a plane containing the incident and reflected light (24 and 28, respectively).

A third problem with operating off-axis is that it typically forces high angles of incidence or large working distances in which to squeeze in optical and mechanical components, while allowing a beam of finite width to propagate without vignetting. Generally speaking, deviating from perpendicularity is never desirable in optical or mechanical systems, as it can produce a coupling between different axes of motion. As an example, in the system drawn in the FIG. 1, deviations in sensor flatness will produce an apparent motion in the direction of beam tilt. The high aspect ratio of the slit 32 helps us again here, requiring only a very narrow beam in the off-axis direction, allowing us to move the prism 18 close to the sensor 12 and to operate only slightly off axis (small angles for angle α, e.g., less than 10 degrees). In the other direction, where the slit is long, the prism can be extended into the direction of the page without limitation, and the focusing components, which will be circularly symmetric, can be sufficiently large to capture the entire field of view.

The arrangement shown in FIG. 1 thus eliminates the need for a beam splitter to direct the incident and reflected light on an optical biosensor. This increases the light efficiency fourfold. It does so while operating on-axis in the direction where the biosensor is sensitive to angle of incidence and where the spatial orientation of the slit will produce minimal error due to the depth of focus of the telecentric lens 30.

In preferred embodiments, we have come to realize that collimating the light from the source 14 very carefully while allowing the telecentric lens 30 to accept a wide angle of light diffracted from the sensor 12 surface by spatially small objects is the right way to design the arrangement of FIG. 1. The collimation optics 16 of FIG. 1 are shown as representative and in simplified form only, and more sophisticated optics for the collimation optics 16 which would reduce the divergence of the incoming collimated light could also be used.

FIG. 3 shows an alternative configuration for the optical arrangement of FIG. 1, in which the prism 18 of FIG. 1 is replaced by two spatially separated mirrors 20 and 22. The first mirror or reflecting surface 20 directs the incident radiation from the light source to the biosensor, and the second mirror or reflecting surface 22 directs the reflected light from the sensor to the telecentric optics 30. The mirrors 20 and 22 are inclined at an angle δ less than 45 degrees. The embodiment of FIG. 3 includes a polarizing filter 50 between the first surface 20 and the biosensor 12. The arrangement of FIG. 3 includes all the benefits of the arrangement of FIG. 1 as compared to prior art beam splitter approaches.

Polarized Light

Note that it is preferred to use polarized light in this system. Polarization could be achieved by placing a film polarizer anywhere in the optical path between the output of the collimation optics and the telecentric lens, and most simply in the illumination path. Alternatively, polarization could be achieved by making one of the reflective surfaces of the prism, such as surface 20, a polarizing dielectric stack. For example, a polarizing filter can be placed between the light source and the first reflecting surface, or between the first reflecting surface and the biosensor. From a practical point of view, it would be best to place it between the collimation optics and the first reflecting surface (mirror or prism surface) so that optical coatings on downstream angled surfaces can be optimized for one axis of polarization or the other. But a system would be completely workable with other positionings of the polarizing filter.

Optical Feedback Sampling Point

Some quantity of light from the collimating optics may pass through the first surface 20, reflect off of the second surface 22 in the interior of the prism and exit the prism at location 36 shown in FIG. 1. This exiting light 38 is a potential sampling point for optical feedback. Optical feedback can be used to control the intensity of the light source 14.

Method of Preventing Interference Fringes

Figure 4:
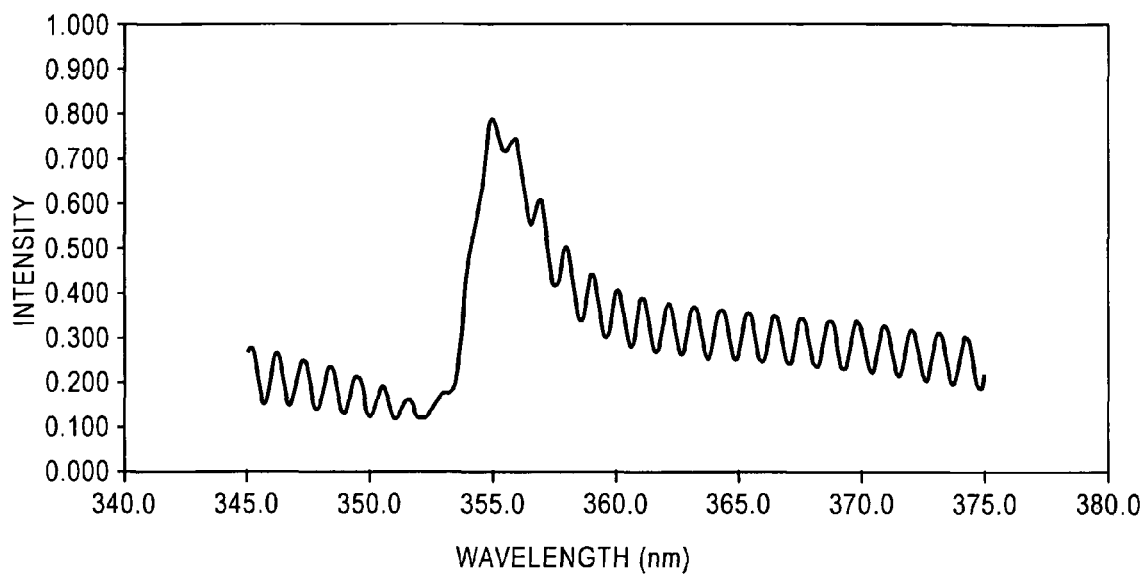
FIG. 4 is a plot of intensity as a function of wavelength showing an example of interference fringes in a clear plate (polyester substrate) for a PC biosensor using normal incident light in a reflection mode.

The photonic crystal sensors of this disclosure modify the spectrum of reflected light based on the index of refraction of material bound to their active surface, and the label-free instrument of FIG. 1 measures the change in this spectrum to determine the degree and/or location of bound material. Because both the bottom surface of the sensor 12 and the upper surface in contact with the sample are reflective, interference of light reflected from these surfaces results in a prominent modulation in the reflected spectrum at intervals equally spaced in optical frequency (which appear at roughly equal spacing in wavelength). This prominent modulation, which is referred to somewhat loosely as interference fringes, obscures slight shifts in wavelength that are the basis of measurements of the sample, rendering such measurement difficult and less precise. An example of this phenomenon is shown in FIG. 4. FIG. 4 is a plot of intensity as a function of wavelength showing an example of interference fringes in a clear plate (polyester substrate) for use in a PC biosensor using normal incident light in a reflection mode. The spectrum is modulated as shown in the Figure due to interference effects.

Heretofore, two approaches have been taken to minimize the effect of the modulation in the spectrum:

1. We have applied a boxcar filter to the sampled spectrum with a filter width equal to the approximate spacing of the fringes. This successfully suppresses the presence of the fringes over a narrow wavelength range where the spacing of the fringes do not vary much in wavelength. The filtering comes at the expense of spectral resolution.
2. We have used a polyester base material for the sensor with a rough matte surface to scatter the reflection from the inactive (lower) surface. See U.S. Pat. No. 7,197, 198. This technique reduces the depth of the fringes, but also reduces the strength of the reflected signal. In addition, the matte surface can reduce spatial resolution in imaging applications due to its scattering property.

There remains a need to reduce or modify the interference fringes of FIG. 4 while avoiding undesirable losses in either spectral or spatial resolution. Surprising, it has been discovered that illuminating the sensor material with incoherent light sources such as LED, white light sources, tungsten lamps, and others by more than a few degrees from normal incidence (as shown in the arrangements of FIGS. 1, 2B and 3) causes the interference fringes to essentially disappear. This happens both in transmission and reflection. The reason underlying this effect is believed to be due to the incoherent nature of the light from such sources, e.g., an LED. As presently understood, in essence there is very poor phase correlation between the rays of light being emitted by different portions of the LED surface and between the rays emitted by a single area into a range of angles. Tilting the angle of incidence relative to the sensor material even slightly spatially displaces the reflected ray from the incident ray, causing the reflected and incident rays that overlap to have no fixed phase relationship between one another, thus eliminating interference. In technical terms, one can define a coherence distance for any source; in other words, the distance across the source from which two rays can be combined and still yield interference. By tilting the sensor (or, equivalently, tilting the angle of incidence away from normal as shown in FIGS. 1, 2B or 3) we appear to be causing the reflected and incident rays to be combined from areas of the LED that exceed its coherence length.

As described earlier in this document in conjunction with in FIGS. 1, 2B and 3, an optical geometry in label-free imager instrument is described to avoid interference fringes as shown in FIG. 4 by designing the instrument wherein the angle of incidence and reflection deviate considerably, from normal, typically from between 3 and 15 degrees, and more preferably between 6 and 12 degrees as indicated by angle α in FIG. 2B. Ten degrees is considered a presently preferred embodiment. The primary purpose of this arrangement is to increase the optical throughput of the instrument without deleterious effects on the optical or spectral resolutions while avoiding undesirable interference fringes. The designs of FIGS. 1 and 3 provides a very simple fix to a problem without changes in the construction of the sensor 12 or its manner of use.

Figure 5:
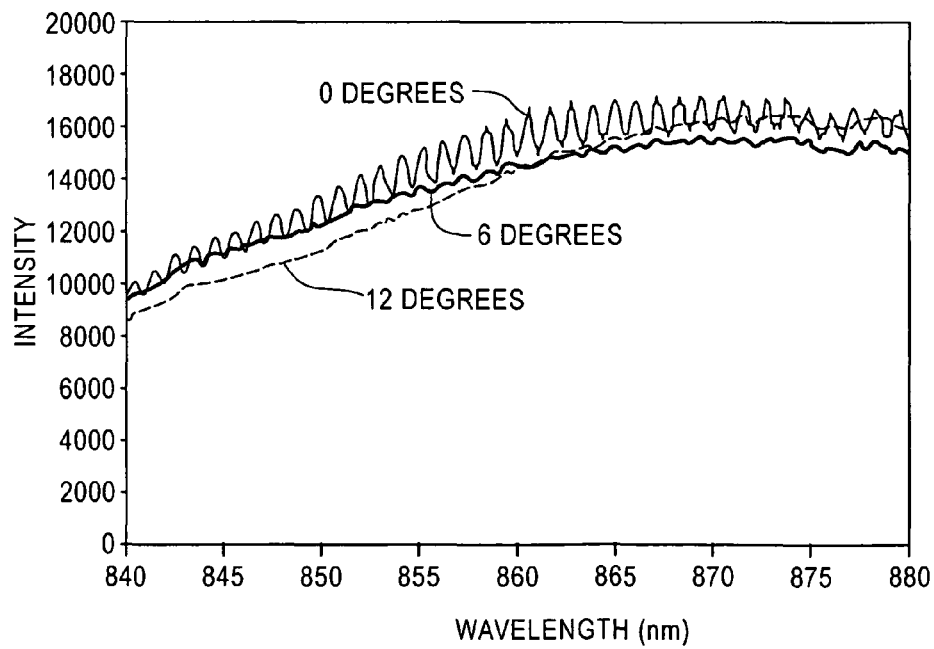
FIG. 5 is a plot of spectrometer counts as a function of wavelength for a label-free biosensor with three different values of angle of incidence (angle α in FIG. 2B), demonstrating the removal of the spectral fringes of FIG. 4 with non-normal angles of incidences of 6 and 12 degrees.

The improvement in eliminating interference fringes are demonstrated in FIG. 5. This Figure is a plot of spectrometer counts as a function of wavelength for a label-free biosensor with three different values of angle of incidence (angle α in FIG. 2B), demonstrating near-total removal of the interference fringes of FIG. 4 with non-normal angles of incidences of 6 and 12 degrees.

In view of the above, in one aspect of this disclosure a method for reducing interference fringes produced in label-free imaging of a photonic crystal biosensor having a periodic grating structure in the form of lines having a direction has been described, comprising the steps of:

providing a light source generating incoherent light (FIG. 1, light source 14);

directing the incoherent light through collimating optics (FIG. 1, 16) and generating collimated the light from the light source;

directing the collimated light onto a surface of the biosensor at a non-normal angle of incidence (FIGS. 1, 3, 2B), and wherein the deviation from normal incidence is chosen to be parallel to the said direction of the lines of the periodic grating structure (FIGS. 2A and 2B);

directing light reflected from the biosensor to telecentric optics (FIG. 1, 30); and directing light from the telecentric optics to a spectrometer (FIG. 1, 34).

In preferred embodiments, the angle of deviation from normal incidence (angle α in FIG. 2B) is between 3 and 15 degrees. In more preferred embodiments, the deviation from normal incidence (angle α) is between 6 and 12 degrees. The incoherent light source (FIG. 14) can take several preferred forms, including a light emitting diode, a tungsten lamp, a halogen lamp, and a xenon arc lamp. The method may also include the step of providing optical feedback control of the intensity of the light source.

Variation from the specifics of the disclosed embodiments is possible without departure from the scope of the invention. All questions concerning scope are to be answered by reference to the appended claims.

I claim:

1. An optical arrangement for illuminating a surface of a biosensor comprising a photonic crystal biosensor having a periodic grating structure in the form of lines having a direction, comprising:
   a light source generating light;
   collimating optics for collimating the light from the light source;
   first and second spatially separated reflecting surfaces, wherein the first reflecting surface receives light from the collimating optics and directs incident light onto a surface of the biosensor and the second reflecting surface receives light reflected from the surface of the biosensor;
   telecentric optics receiving light from the second reflecting surface; and
   a spectrometer having an entrance slit receiving light from the telecentric optics.

2. The optical arrangement of claim 1, wherein the incident light impinges upon the biosensor surface at a non-normal angle of incidence.

3. The optical arrangement of claim 2, wherein the deviation from normal incidence is chosen to be parallel to the direction of the grating lines on the sensor.

4. The optical arrangement of claim 1, wherein the entrance slit has a very high aspect ratio of greater than 100 to 1.

5. The optical arrangement of claim 1, wherein the telecentric optics form an image of the entrance slit on the biosensor surface and the image of the entrance slit on the biosensor surface is oriented perpendicular to a plane containing the incident and reflected light.

6. The optical arrangement of claim 1, wherein one of the first surface or the second surface comprises a polarizing dielectric stack.

7. The optical arrangement of claim 1, further comprising a polarizer in the optical path between the output of the collimation optics and the telecentric lens.

8. The optical arrangement of claim 1, wherein the light source comprises a quasi-point source.

9. The optical arrangement of claim 1, wherein the light source comprises a noncoherent light source.

10. The optical arrangement of claim 9, wherein the light source is selected from the group of light sources consisting of a light emitting diode, a tungsten lamp, a halogen lamp, and a xenon arc lamp.

11. The optical arrangement of claim 1, further comprising a sampling point for optical feedback control of the intensity of the light source.

12. The optical arrangement of claim 1, wherein the first and second spatially separated reflecting surfaces comprise first and second surfaces of a non-right angle prism.

13. The optical arrangement of claim 12, wherein the first surface comprises a polarizing dielectric stack.

14. The optical arrangement of claim 12 wherein the first and second surfaces are inclined at an angle less than 45 degrees.

15. The optical arrangement of claim 1, wherein the first and second surfaces comprise first and second spatially separated mirrors.

16. The optical arrangement of claim 15 wherein the first and second surfaces are inclined relative to the direction of a beam from the collimating optics at an angle less than 45 degrees.

17. The optical arrangement of claim 12, further comprising a polarizing filter positioned in the optical path between the collimating optics and the first surface of the prism.

18. The optical arrangement of claim 15, further comprising a polarizing filter positioned in the optical path between the collimating optics and the first mirror.

19. The optical arrangement of claim 1, wherein the light source comprises an incoherent source, wherein the incident light impinges upon the biosensor surface at a non-normal angle of incidence, wherein the deviation from normal incidence is chosen to be parallel to the direction of the grating lines on the sensor.

20. The optical arrangement of claim 1, wherein the angle of deviation from normal incidence (angle α) is between 3 and 15 degrees.

21. The optical arrangement of claim 20, wherein the angle of deviation from normal incidence (angle α) is between 6 and 12 degrees and wherein the light source is selected from the group of light sources consisting of a light emitting diode, a tungsten lamp, a halogen lamp, and a xenon arc lamp.

22. A method for reducing interference fringes produced in label-free imaging of a photonic crystal biosensor having a periodic grating structure in the form of lines having a direction, comprising the steps of:
   providing a light source generating incoherent light;
   directing the incoherent light through collimating optics and generating collimated the light from the light source;
   directing the collimated light onto a surface of the biosensor at a non-normal angle of incidence, and wherein the deviation from normal incidence is chosen to be parallel to the said direction of the lines of the periodic grating structure;
   directing light reflected from the biosensor to telecentric optics; and
   directing light from the telecentric optics to a spectrometer.

23. The method of claim 22, wherein the angle of deviation from normal incidence (angle α) is between 3 and 15 degrees.

24. The method of claim 23, wherein the deviation from normal incidence (angle $\alpha$) is between 6 and 12 degrees.

25. The method of claim 22, wherein the light source is selected from the group of light sources consisting of a light emitting diode, a tungsten lamp, a halogen lamp, and a xenon arc lamp.

26. The method of claim 22, further comprising the step of providing optical feedback control of the intensity of the light source.

* * * * *